US011125744B2

(12) United States Patent
Van Roosmalen et al.

(10) Patent No.: US 11,125,744 B2
(45) Date of Patent: Sep. 21, 2021

(54) DEVICE, SYSTEM AND METHOD FOR DETECTING AN ANALYTE IN A BODY FLUID SAMPLE CONTAINING A PLURALITY OF CELLS

(71) Applicant: SIEMENS HEALTHINEERS NEDERLAND B.V., The Hague (NL)

(72) Inventors: Markus Hendrikus Van Roosmalen, Berkel-Enschot (NL); Jeroen Hans Nieuwenhuis, Waalre (NL); Per Venge, Uppsala (SE)

(73) Assignee: SIEMENS HEALTHINEERS NEDERLAND B.V., The Hague (NL)

( * ) Notice: Subject to any disclaimer, the term of this patent is extended or adjusted under 35 U.S.C. 154(b) by 121 days.

(21) Appl. No.: 16/308,865

(22) PCT Filed: Jun. 26, 2017

(86) PCT No.: PCT/EP2017/065648
§ 371 (c)(1),
(2) Date: Dec. 11, 2018

(87) PCT Pub. No.: WO2018/001932
PCT Pub. Date: Jan. 4, 2018

(65) Prior Publication Data
US 2019/0154671 A1   May 23, 2019

(30) Foreign Application Priority Data

Jun. 30, 2016 (EP) .................................... 16177241
Nov. 25, 2016 (EP) .................................... 16200668

(51) Int. Cl.
G01N 33/74 (2006.01)
G01N 33/543 (2006.01)
(Continued)

(52) U.S. Cl.
CPC . G01N 33/54306 (2013.01); G01N 33/54326 (2013.01); G01N 33/54393 (2013.01);
(Continued)

(58) Field of Classification Search
CPC ....... G01N 33/54306; G01N 33/54326; G01N 33/54393; G01N 33/57496; G01N 33/74; G01N 33/56972; G01N 2800/26
See application file for complete search history.

(56) References Cited

U.S. PATENT DOCUMENTS 3,850,752 A   11/1974   Schuurs
3,901,654 A   8/1975    Gross
(Continued)

FOREIGN PATENT DOCUMENTS

CN   202916284 U   5/2013
WO   2008107827 A1   9/2008
(Continued)

OTHER PUBLICATIONS

Sharif et al. Novel Immunoassay technique for rapid measurement of intracellular proteins using paramagnetic particles. Journal of Immunological Methods 388: 78-85 (2013)—IDS.*
(Continued)

*Primary Examiner* — Gailene Gabel (57) ABSTRACT

The present invention relates to a device (100) for detecting an analyte (12) in a body fluid sample (14) containing a plurality of cells (16). The device (100) comprises a sample input (18) for receiving a body fluid sample (14) containing a plurality of cells (16), and an immunoassay unit (20) comprising a detection surface (28) for performing an immunoassay of said body fluid sample (14) containing a plurality of cells (16). The immunoassay unit (20) comprises an activating reagent (22) for activating the plurality of cells (16) contained in the body fluid sample (14) to release an
(Continued)

analyte (12), an anti-analyte-antibody (24) capable of binding to said analyte (12) to form a complex (26) comprising said anti-analyte-antibody (24) and said analyte (12), wherein the forming of said complex (26) proceeds at least partially simultaneous to the activating of said plurality of cells (16).

15 Claims, 5 Drawing Sheets

(51) Int. Cl.
    *G01N 33/574* (2006.01)
    *G01N 33/569* (2006.01)

(52) U.S. Cl.
    CPC . *G01N 33/56972* (2013.01); *G01N 33/57496* (2013.01); *G01N 33/74* (2013.01); *G01N 2800/26* (2013.01)

(56) References Cited

U.S. PATENT DOCUMENTS

| | | | |
|---|---|---|---|
| 3,935,074 | A | 1/1976 | Leute |
| 3,984,533 | A | 10/1976 | Uzgiris |
| 3,996,345 | A | 12/1976 | Schwarzberg |
| 4,034,074 | A | 7/1977 | Miles |
| 4,098,876 | A | 7/1978 | Piasio |
| 4,376,110 | A | 3/1983 | David |
| 4,452,901 | A | 6/1984 | Gordon |
| 6,136,526 | A | 10/2000 | Venge |
| 2004/0115728 | A1 | 6/2004 | Villanueva |
| 2010/0266563 | A1 | 10/2010 | Humes |

FOREIGN PATENT DOCUMENTS

| | | |
|---|---|---|
| WO | 2010035204 A1 | 4/2010 |
| WO | 2014195899 A1 | 12/2014 |
| WO | 2016079219 A1 | 5/2016 |

OTHER PUBLICATIONS

Sharma et al. Point-of-Care Diagnostics in Low Resource Settings: Present Status and Future Role of Microfluidics. Biosensors 5: 577-601 (2015).*
Per Venge et al. (Human Neutrophils lipocalin in fMLP-activated whole blood as a diagnostic means to distinguish between acute bacterial and viral infections. Journal of Immunological Methods 424: 85-90 (May 20, 2015))—IDS.*
Bruls et al. Rapid integrated biosensor for multiplexed immunoassays based on actuated magnetic nanoparticles. Lab on Chip. 9: 3504-3510 (2009).*
Shariff et al. (Novel Immunoassay technique for rapid measurement of intracellular proteins using paramagnetic particles. Journal of Immunological Methods 356: 78-85 (Dec. 14, 2012))—IDS.*
Venge, Per et al "Human Neutrophillipocalin in fMLP-Activated Whole BLood as a Diagnostic means to distinguish between acute bacterial and viral infections", Journal Immunological Methods, vol. 424, pp. 85-90, 2015.
Alere Triage Ngal Test—Point of Care or Laboratory Testing, 2015.
Sharif, Elham et al "Novel Immunoassay Technique for Rapid Measurement of Intracellular Proteins using Paramagnetic Particles", Journal of Immunological Methods, vol. 388, No. 1-2, Feb. 2013, pp. 78-85.
Eyer, K. et al "Implementing Enzyme-Linked Immunosorbent Assays on a Microfluidic Chip to Quantify Intracellular Molecules in Single Cells", Analytical Chemistry, vol. 85, No. 6, Mar. 2013, pp. 3280-3287.
Shirasaki, Yoshitaka et al "Real-Time Single-Cell Imaging of Protein Secretion", Scientific Reports, vol. 4, Apr. 2014.
Tkac, Jan et al "Evaluation of Distruption Methods for the Release of Intracellular Recombinant Protein from *Escherichia coli* for Analytical Purposes", Biotechnology and Applied Biochemistry, vol. 40, No. 1, Aug. 2004, pp. 83.
Venge, Per et al "Human Neutrophil Lipocalin as a Superior Diagnostic means to Distinguish between Acute Bacterial and Viral Infections", Clinical and Vaccine Immunology, vol. 22, No. 9, Sep. 2015, pp. 1025-1032.

* cited by examiner

DEVICE, SYSTEM AND METHOD FOR DETECTING AN ANALYTE IN A BODY FLUID SAMPLE CONTAINING A PLURALITY OF CELLS

CROSS-REFERENCE TO PRIOR APPLICATIONS

This application is the U.S. National Phase application under 35 U.S.C. § 371 of International Application No. PCT/EP2017/065648, filed on Jun. 26, 2017, which claims the benefit of European Patent Application No. 16177241.3, filed on Jun. 30, 2016 and European Patent Application No. 16200668.8, filed on Nov. 25, 2016. These applications are hereby incorporated by reference herein.

FIELD OF THE INVENTION

The present invention relates to a device, a system and a method for detecting and, preferably, analyzing an analyte in a body fluid sample containing a plurality of cells e.g. a whole blood sample.

BACKGROUND OF THE INVENTION

Most of the diagnostic decisions are based on information provided by blood testes. However, such tests are often problematic because it can take hours to get the result from a central laboratory. In many instance the analyte is not available in whole blood samples but being part of the blood cells. This analyte can only be measured after pretreatment of the cell fraction. This pre-treatment can be time-consuming and from there expensive. Moreover it often requires complex instruments and a relatively high degree of skill on the part of the person performing the analysis. Those tests which need a long pre-treatment are not suitable in threatening conditions where speed and high sensitivity are essentially required.

In the field of clinical diagnostic "point of care (POC) devices" were used to detect analyte in bodily fluid samples including saliva, whole blood, blood serum, blood plasma, urine and so on without pre-treatment of the bodily fluids. These so called "Minicare" devices are easy to use. Only a small sample like a drop of blood is required to get accurate and quick results within minutes. The analyte is often a biomarker such as proteins, peptides, hormones, DNA, RNA or enzymes for special diseases. These tests are well known in the art. The test itself can be a simple test strip or built in an analyzing system as a disposable cartridge. The main difficulty is to measure very low concentration (picomolar) of molecules in a small sample volume (e.g. a drop of blood) within minutes to get accurate results.

The test is often done by allowing the molecule to interact in a biochemical reaction, which directly or indirectly results in a detectable signal, e.g. color indication on a test stripe. One widely used assay is the immunoassay to determine the presence or absence as well as the concentration of specific analyte in various samples through the use of specific antibodies. Immunoassays can be done heterogeneous in a multi-step assay with washing- and separation-steps, or homogeneous by incubating the reagents and the sample for a define time and afterwards detecting the antibody-antigen complex. The use of homogeneous or heterogeneous assay is dependent, in particular but without limitation on the specific analyte. The main problem still residue in the fact, that each analyte, which should be detected, a specific immunoassay has to be developed because of the need of specific antibodies.

At the moment, there is still no possibility to measure very low concentration of an analyte, which is part of the cell fraction, in a fast immunoassay. The main practical problems still reside in the fact that a time consuming pre-treatment of the body fluid sample is necessary before running the immunoassay.

One example of a specific target molecule which can only be measured after pre-treatment is the biomarker HNL (Human neutrophil lipocalin). HNL is part of the cell fraction and can only be measured when stimulated neutrophils excrete the analyte. HNL is used as a high sensitive biomarker for inflammatory by bacterial infections. Such measurement is of interest in the distinction between various causes of acute infections, since the levels of HNL are highly raised in serum or plasma in patients with acute bacterial infections as opposed to the findings in patients with acute viral infections. From there it is possible to distinguish between bacterial and viral infections in patients which results in the reduction of antibiotics abuse.

Venge, Per et al. (J. Immunol. Methods 424 (2015) 85-90) describe a method for quantitating HNL count in heparinized whole blood. However, therefore it is necessary to pre-treat the whole blood sample with fMLP (N-Formylmethionyl-leucyl-phenylalanine) for 20 minutes before measuring the HNL concentration in an immunoassay.

Accordingly, there is a need for a biological assay, which is faster and more cost efficient than the biological assays that are known in the art.

SUMMARY OF THE INVENTION

It is an object of the present invention to provide a device, a system and a method which enable detection and, preferably, analysis of an analyte in a body fluid sample in a fast manner, e.g. less than 10 minutes, where cells contained in the body fluid sample are still viable while running the detection of the analyte. Therefore, the analysis of an analyte has to proceed without a time consuming pre-treatment wherein the conditions in the device have to be in an osmotic friendly manner to secure the viability of the cells to further help forming a diagnostic decision. Another object of the invention is avoiding additional method steps.

In a first aspect of the present invention a device for detecting an analyte in a body fluid sample containing a plurality of cells is presented comprising a sample input for receiving a body fluid sample containing a plurality of cells, and an immunoassay unit comprising a detection surface for performing an immunoassay of said body fluid sample containing a plurality of cells, wherein said immunoassay unit comprises an activating reagent for activating the plurality of cells contained in the body fluid sample to release an analyte, and an anti-analyte-antibody capable of binding to said analyte to form a complex comprising said anti-analyte-antibody and said analyte, wherein the forming of said complex proceeds at least partially simultaneous to the activating of said plurality of cells.

In a second aspect of the present invention a system for detecting an analyte in a body fluid sample containing a plurality of cells is presented comprising a device for detecting an analyte in a body fluid sample containing a plurality of cells, a light source for projecting light at the detection surface of the immunoassay unit of said device, a detection unit for receiving reflected light from the detection surface of said immunoassay unit, and an analyzer for analyzing the reflected light detected by the detection unit.

In yet further aspects of the present invention, there is provided a corresponding method, for detecting an analyte in a body fluid sample containing a plurality of cells is presented comprising receiving a body fluid sample containing a plurality of cells, and performing an immunoassay of said body fluid sample containing a plurality of cells, including activating the plurality of cells contained in the body fluid sample to release an analyte, forming a complex comprising an anti-analyte-antibody and said analyte, wherein the forming of said complex proceeds at least partially simultaneous to the activating of said plurality of cells, and detecting formation of said complex.

Preferred embodiments of the invention are defined in the dependent claims. It shall be understood that the claimed system and method, have similar and/or identical preferred embodiments as the claimed device, in particular as defined in the dependent claims and as disclosed herein.

The present invention is based on the idea of activating cells of a body fluid sample to release an analyte and performing an immunoassay in a one pot reaction. This offers the advantages over the current state of the art to perform an immunoassay with an analyte which is not available in solution from the outset. The inventors have found that when changing the buffer formulation of the immunoassay into a defined osmotic friendly formulation, the cells are still viable while they were activated by the activating reagent. Hence, it is possible to run an immunoassay faster, without any time consuming pre-treatment of the body fluid sample. The present invention further more offers an immunoassay which is sensitive in the picomolar range although only a sample volume e.g. less than 30 µl is needed.

The term "analyte" also referred as "target molecule" or "antigen", as used herein, shall refer to any molecule of which concentration or presence as such is to be determined. Examples of analyte are biomarker such as proteins, peptides, hormones, DNA, RNA or enzymes. The analyte is inside the cells. Therefore, the cells have to be activated to release the analyte before performing the immunoassay without lysing itself. Therefore, the cells have to stay viable while performing the immunoassay.

The term "body fluid sample" is used in a broad sense herein and is intended to include a wide range of biological materials which contains a plurality of cells. The sample may be any suitable fluid in which the analyte is part of the cells. Such body fluid sample can be saliva, urine or whole blood sample.

The term "immunoassay" refers to any various immunoassays known in the art. It is not limited to: competitive and non-competitive assay systems using techniques such as radioimmunoassay, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), Western blots, precipitation reactions, agglutination assays (e.g., gel agglutination assays, hemagglutination assays), immunofluorescence assays, protein A assays, and immunoelectrophoresis assays, etc., as well as, e.g. devices for detection of analyte that involve magnetic based separation of the analyte of interest.

The term "activating reagent", as used herein, shall refer to a molecule that is being able to activate cells in order to release an analyte which is inside the cells contained in a body fluid sample without lysing the cells itself.

The term "activation", as used herein, shall refer to a stimulation that stimulates the plurality of cells to release an analyte. Furthermore, activation refers to a stimulation of a signal transduction pathway inside the cells leading to the respiratory burst of the analyte induced by the activating reagent. Therefore, the activating reagent may play a regulatory role in the signal transduction pathway. To activate a cell, the activating reagent may bind to cell surface receptors. When binding to the receptor a wide variety of intracellular signaling pathways mediated by e.g. phosphatidylinositol-specific phospholipase C (PLC), phospholipase $A_2$, phospholipase D (PLD), phosphatidylinositol 3-kinase (PI3K), and mitogen-activated protein kinases (MAPKs) will be activated to induce various cellular functions.

The term "anti-analyte-antibody", as used herein, shall refer to a binding molecule which is being able to bind specifically to the analyte. The anti-analyte-antibody or functional fragment thereof may be derivatized, for example with a fluorescent moiety, a radioactive moiety a chromogenic substrate, and the like.

The term "anti-analyte-antibody" is used in the broadest sense and includes fully assembled antibodies, monoclonal antibodies, polyclonal antibodies, multispecific antibodies (including bispecific antibodies), antibody fragments that can bind an antigen (including, Fab', F'(ab)2, Fv, single chain antibodies, diabodies), and recombinant peptides comprises the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated.

The term "proceeds at least partially simultaneous", as used herein, shall not refer to the starting points of the reactions. The reactions of building the antigen-antibody-complex can only start when all requirements are available. The building of the complex can only start when the analyte is solved.

The reagents for performing an immunoassay are already present within the immunoassay unit. The user of the device only needs to add the body fluid sample into the sample input. When the body fluid sample achieves the immunoassay unit, the activating reagents and anti-analyte-antibodies will be solved and produce the intended buffer conditions. Partially simultaneous the reagents start to react with the cells and molecules which are part of the sample. The dry reagents of the immunoassay unit include the buffer components necessary for the assay e.g. the anti-analyte-antibodies. The reagents can be deposited via several drying techniques including lyophilization. Lyophilization prevents the formation of crystals and allows the reagents to be dried to an amorphous glassy state that is readily redispersed upon the addition of a fluid. When the body fluid sample achieves the immunoassay unit, the activating reagents and anti-analyte-antibodies will be solved and start to react with the cells and molecules which are part of the sample. Because of the stored dry form of the components, a generally longer durability of the device especially of the reagents is achieved.

Before the immunoassay can start, the analyte which is inside the cells has to be released. Therefore, the cells have to be activated. As soon as the first analyte is solved outside the cells, the immunoassay can start with forming a complex. This is advantageously because the activating and the immunoassay proceeds partially at the same time, therefore both reactions enable fast.

The term "detection surface" as used herein, refers to a surface to which antibodies can be coupled and which allows the detection of antibody-antigen-complex. Typically, the detection surface is a solid, uniform surface. The detection surface can be involved in detection as a detection unit. Alternatively, the detection unit can be located in the vicinity e.g. under the detection surface, allowing detection of antibody-antigen-complex present close to the detection surface. Examples of suitable surfaces include, glass, metal, plastic, an organic crystal or an inorganic crystal (e. g. silicon), an amorphous organic or an amorphous inorganic material (e. g. silicon nitride, silicon oxide, silicon oxinitride, aluminum oxide). Suitable surface materials and linking chemistries are known to the person skilled in the art.

Detection means suitable for use in the device, systems and method of the present invention are detection means capable of detecting the relevant signal such as, but not limited, to a magnetic signal, magnetoresistance, a Hall effect, an optical signal (reflection, absorption, scattering, fluorescence, chemiluminescence, RAMAN, FTIR, etc.). Such optical labels are known to the skilled person and include fluorescein dyes, such as 5- (and 6-) carboxy-4',5'-dichloro-2',7'-dimethoxy fluorescein, 5-carboxy-2',4',5',7'-tetrachlorofluorescein and 5-carboxyfluorescein, rhodamine dyes such as 5- (and 6-) carboxy rhodamine, 6-carboxytramethyl rhodamine and 6-carboxyrhodamine X, phthalocyanines such as methyl, nitrosyl, sulphonyl and amino phthalocyanines, azo dyes, azomethines, cyanines and xanthines such as the methyl, nitro, sulphano and amino derivatives, and succinylfluoresceins. Other suitable labels are fluorophores from the group of cyanine dimers and monomers, such as TOTO, YOYO, TO-PRO, Cy3, Cy5, Cy5.5, Cy7 etc., or dyes such as LCRed 705 may be used as the fluorescent dye.

The term "light source" as used herein, refers to light source that emitting light into the sample volume. The light source may for example be a laser diode or an LED.

The term "detection unit" as used herein, refers to a light detector (photodetector) that detect reflected light that has interacted with the body fluid sample, particular reflected light that has been scattered by the antibody-antigen complex. Observing scattered light has the advantage that its amount (intensity) is proportional to the amount of scattering components. Small quantities of these components can therefore optimally be tackled with highly sensitive light detectors, because there is no high baseline signal that has to be dealt with. The detection unit may comprise for example photodiodes, photo resistors, photocells, a CCD chip or a photo multiplier tube.

The term "analyzer" as used herein, refers to an evaluation unit, which is connected to the detection unit for analyzing the information of the detection unit.

In a preferable embodiment, the anti-analyte-antibody is a first anti-analyte-antibody and said complex is a first complex, wherein said immunoassay unit further comprises a second anti-analyte-antibody which is immobilized on the detection surface, capable of binding to said first complex to form a second complex comprising said first anti-analyte-antibody, said analyte and said immobilized second anti-analyte-antibody, wherein the forming of said second complex proceeds at least partially simultaneous to said forming of the first complex. Therefore, the immunoassay is performed in a so called "sandwich immunoassay".

In a preferable embodiment, the immunoassay unit further comprises a buffer reagent. "Buffer reagent" may generally be understood as a plurality of reagents that define an osmotic friendly solution and have a pH stabilizing effect e.g. buffer reagents like Hepes, proteins like BSA and/or BGG, salts, sugars and enzyme inhibitors. Hence, viability of the plurality of cells can be maintained during the activation of the cells and the immunoassay. This leads to an osmotic balance conditions within the assay. When cells lyse the sample will dilute and therefore falsify the results of the assay.

In another preferable embodiment, the buffer reagents comprise at least one reagent of sugar and salt. The buffer reagents preferably assist in the biological interactions especially maintain cell viability which includes a balanced osmotic pressure. With the use of different types and different amounts of sugar the osmotic conditions of the body fluid sample can be adapted in a preferred way. The use of salt also determines the osmotic conditions in the body fluid sample. Salt is a suitable source of positive and negative counter ions. It is important that a suitable salt content is adjusted otherwise more cells will lyse by under- or overvaluing the salt content.

In a preferable embodiment, the salt is selected from the group of potassium bromide, potassium chloride, potassium iodide and/or potassium thiocyanate and a combination thereof. Potassium in its solved form $K^+$ is preferred in the use as a positive counter ion in immunoassays.

In a preferable embodiment, the sugar is a polysaccharide, in particular selected from the group of dextran, CM-dextran and a combination thereof. The use of sugar with a high molecular weight will lead to better osmotic balances of the cells contained in the body fluid sample in comparison to the use of mono- or disugars. A high better osmotic balance of the cells is preferred because it contributes to the viability of the cells.

In another preferable embodiment, the activating reagent is an N-formyl-peptide, preferably N-Formylmethionyl-leucyl-phenylalanine (fMLP) and/or Protein A and/or Lipopolysaccharide (LPS) and/or platelet-activating factor and/or an unmethylated CpG oligodinucleotide and/or tumor necrosis factor (TNF). This embodiment advantageously enables a selectively activation of the cells especially the neutrophil cells to secrete the analyte while the cells stay viable. The activation of the cells proceeds without any interaction of the activating reagent with the compounds of the immunoassay, especially the anti-analyte-antibodies.

In another preferable embodiment the analyte is a protein, preferably a lipocalin, in particular Human Neutrophil Lipocalin (HNL). This embodiment advantageously enables diagnose of bacterial infection. HNL is a diagnostic marker for identifying inflammation. Levels of HNL in patients with viral infections are similar to those found in healthy subjects. However, when a bacterial infection is present, the HNL concentration is increased. Thus, the use of HNL can be used as a biomarker for a device that distinguishes between bacterial and viral infection.

In a preferable embodiment, the anti-analyte-antibody is coupled to a magnetic particle. This embodiment advantageously enables a shorter reaction time of the immunoassay because of the manipulation of the bound anti-analyte-antibodies inside the immunoassay unit. This embodiment is further advantageous since the magnetic properties of magnetic particles themselves can be used for detection purposes.

The detection of magnetic particles at a detection surface can be ensured by any direct or indirect method known in the art. Particular detection methods are based on the magnetic properties of the particle such as GMR or on optical properties of the magnetic particles, such as detection with frustrated total internal reflection (FTIR).

This embodiment is further advantageous, since the reflected light that has interacted with the body fluid sample often comprises light that was scattered by complex of interest as well as by other agglomerates. To separately determine those components of reflected light that relate to complex of interest, these complex is actuated in a particular way by the magnetic actuation field, which results in a corresponding characteristic modulation of their reflected light components.

Suitable magnetic particles include completely inorganic particles and particles which are a mixture of an inorganic and an organic material e.g. a polymer.

Attachment of the anti-analyte-antibody according to the invention to the surface of a magnetic particle can be performed by methods described in the art. Magnetic particle are available in various size, ranging from nanometers to micrometers. When considering the magnetic particle size to employ in a high sensitivity assay, it is important to weight the counteracting effects. The larger the particle the higher is the signal per binding event. Moreover, large magnet particles imply larger magnetic content which in turn allow a large force to be applied for a given magnetic field. This permits the particles to be collected and moved through the solution with a greater speed. On the other hand large magnetic particles have a tendency to irreversibly aggregate and are more sterically hindered when they bind to a surface. In addition, large particle reduce the dynamic range and the quantity of the assay, as the packing number of particles on the detection surface is limited for larger particles.

This embodiment is further advantageous, since the so-called "Magnotech" technology can be used for the detection of an analyte in a body fluid sample. This method preferably comprises the following successive steps:

1. Mobile reagents (activating reagents, anti-analyte-antibody), previously stored in a dry state within the immunoassay unit of the device, are mixed with the body fluid sample containing a plurality of cells.

2. The activating reagent activates the plurality of cells contained in the body fluid sample to release the analyte. More analyte in body fluid sample results in more anti-analyte-antibodies capturing, i.e. reacting with this analyte to form a complex comprising the anti-analyte-antibody and the analyte.

3. The magnetic particles coupled to the anti-analyte-antibodies of the mobile reagents are then attracted to the detection surface by application of an attractive magnetic field. A certain number of anti-analyte-antibodies may be bound to the detection surface or a certain number of mobile anti-analyte-antibodies (each one may covalently be bound to a magnetic particle) are attached to immobilized anti-analyte-antibodies to form complexes (sandwich assay). The number of these complexes is proportional to the number of the analyte in the body fluid sample.

4. The non-bound reagents are washed from the detection surface by application of a magnetic field directed away from the surface, and only the bound complexes remain accordingly on the detection surface.

5. A light beam is then emitted on the back side of the detection surface at an angle greater than the critical angle, causing a total internal reflection (TIR). The reflected light is then detected. Where TIR takes place, a simultaneous evanescent field is naturally created in the vicinity of the front side of the detection surface. This evanescent field is scattered and absorbed by each bonded complex (by the magnetic particle of each bonded complex): the corresponding reflected light becomes "frustrated". As a consequence, the detection of the frustrated total internal reflection (FTIR) gives an indication of the number of analytes/anti-analyte-antibody-complexes that are bonded to the detection surface. It is to be noted that, according to this Magnotech® technology, the magnetic particles act both as means for manipulating the analyte and label for the optical detection.

6. An algorithm allows then to assess the number of analyte in body fluid sample, based on FTIR detection and predetermined calibration data that have been stored in the device.

In a preferable embodiment, the first anti-analyte-antibody and/or the second anti-analyte-antibody are selected from the group of monoclonal and/or polyclonal antibody, in particular an antibody specific for HNL. The monoclonal antibody according to the present invention also includes Fab fragments from monoclonal antibodies, aptamers, affibodies, scFv fragments and any other single epitope binding moiety known to the person skilled in the art. The polyclonal antibody according to the present invention also includes Fab fragments from polyclonal antibodies, and any group of binding moieties with variable structure known to the person skilled in the art.

In a preferable embodiment, the body fluid sample is a whole blood sample. The term "whole blood sample", as used herein, shall refer to a blood sample comprising viable red and white blood cells as well as blood plasma. This embodiment advantageously enables a fast analyzing of blood samples without a time consuming pre-separating of the cell fraction from the plasma.

In a preferable embodiment, the system further comprises a magnetic field for controlling the magnetic particles. This embodiment advantageously enables manipulating the magnetic particles with the bound anti-analyte-antibodies to bind to the analyte. Therefore, the immunoassay can proceed faster.

The magnetic field may be arranged as magnetic coils. Therefore, two bottom magnets may be arranged below the detection surface according to a "horseshoe" arrangement and a top magnet may be located above the device.

In a preferable embodiment, the system may further comprise an elongated open cavity for receiving the device, electronic circuitry to process and store data and a heating element formed by a metal plate (about 2×5 $cm^2$), provided at each end with electrical resistance, and located above the device at the level of the top magnet.

According to the proposed method the formation of said complex is detected. This may include, in an embodiment of the proposed method, detecting the presence or absence of labels on a detection surface.

According to a further refinement of the invention, said device, system or a method of the invention, the analyte to be detected is inside the plurality of cells, the activating reagent or activating step is more specifically configured to activate the plurality of cells contained in the body fluid sample to release an analyte from inside the plurality of cells without lysing the cells itself, and said anti-analyte-antibody is more specifically configured to bind to said analyte.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
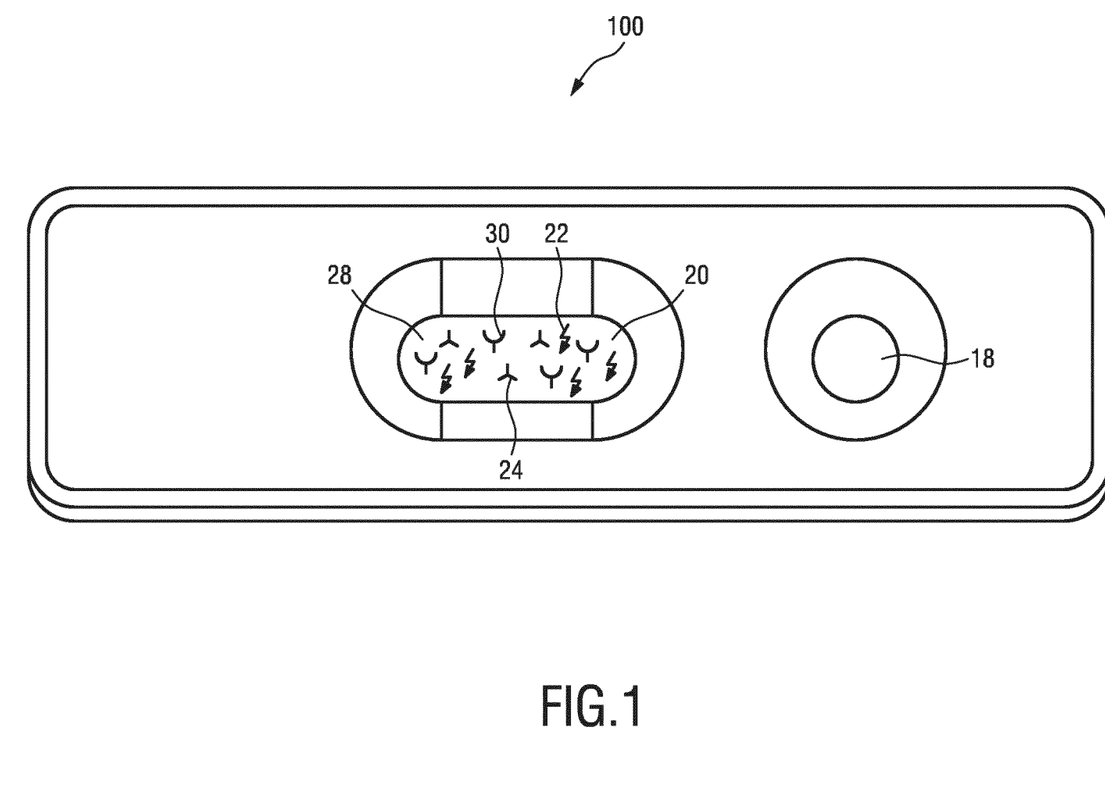
FIG. 1 shows a first embodiment of a device in accordance with the present invention.

FIG. 1 shows a first embodiment of a device 100 in accordance with the present invention. The device 100 shown in FIG. 1 comprises a sample input 18 for receiving a body fluid sample. Besides the sample input 18 the device 100 further comprises an immunoassay unit 20 for performing an immunoassay of the body fluid sample containing a plurality of cells. The input 18 and the unit 20 are preferably connected with each other so that the body fluid sample, for example a droplet of blood, can flow from the sample input 18 to the immunoassay unit 20.

The immunoassay unit 20 comprises an activating reagent 22 for activating the plurality of cells contained in the body fluid sample to release an analyte. The immunoassay unit 20 further comprises an anti-analyte-antibody 24 capable of binding to the analyte to form a complex comprising the anti-analyte-antibody 24 and the analyte, wherein the forming of said complex proceeds at least partially simultaneous to the activating of said plurality of cells (not shown).

The immunoassay unit 20 further comprises a detection surface 28. The detection surface 28 is preferably located at the bottom side of the device 100.

The activating reagents 22 and anti-analyte-antibodies 24 are preferably present in dry form, alternatively dissolved. When the body fluid sample achieves the immunoassay unit 20, the reagents will be solved. In addition to these reagents the immunoassay unit 20 preferably comprises buffer reagents, which define an osmotic friendly solution especially for the cells and stabilize the pH-value.

Accordingly to a preferable embodiment of the present invention the buffer reagent comprises at least one reagent of sugar and salt. The salt may be selected from the group of potassium bromide, potassium chloride, potassium iodide and/or potassium thiocyanate and a combination thereof.

When the immunoassay unit 20 is filled with the body fluid sample the concentration may be of about 0 to 100 mM of buffer, 0 to 25% (w/v) of sugar, typically in a concentration of about 25 to 75 mM of buffer and 1 to 7.5% (w/v) of sugar. Besides these reagents the buffer reagents preferable comprise carrier proteins in a range of 0 to 10%, typically in a concentration of 1 to 7.5% to increase stability of the cells.

In particular embodiments the buffer is a phosphate buffer, the sugar is sucrose and/or a polysaccharide (from the group of dextran, CM-dextran and a combination thereof) and the carrier protein is BSA (Bovine Serum Albumin). Besides other biological buffers such as MES, Bis-Tris, ADA, Aces, PIPES, MOPSO, Bis-Tris Prpan, BES, TES, HEPES, DIPSO, MOBS, TAPSO, Trizma, HEPPSO, POPSO, TEA, EPPS, Tricine, Gly-Gly Bicinie, HEPBS, TAPS, AMPD, TABS or AMPSO can be used.

According to certain embodiments, the volume of the immunoassay unit 20 is between 0.1 and 5 µl, more particularly between 0.5 and 2 µl e.g. 1 µl.

The immunoassay unit 20 is preferable not limited in one chamber. In a preferable embodiment the device 100 comprises more than one immunoassay unit for running more than one immunoassay of the same or different analyte parallel. In this embodiment the sample is spread over different immunoassay units.

In a preferable embodiment the activating reagent 22 may be an N-formyl-peptide, more preferably the tri-peptide fMLP. Also preferably envisaged is the use of Protein A. The present invention further envisages the use of additional alternative neutrophil activators such as Lipopolysaccharide (LPS), platelet-activating factor, an unmethylated CpG oligodinucleotide, or tumor necrosis factor (TNF). These activators may be used alone or in any combination, for instance in the form of fMLP and/or Protein A and/or Lipopolysaccharide (LPS) and/or platelet-activating factor and/or an unmethylated CpG oligodinucleotide and/or tumor necrosis factor (TNF), such as e.g. fMLP in combination with Protein A, fMLP in combination with LPS, fMLP in combination with platelet-activating factor, fMLP in combination with unmethylated CpG oligodinucleotide, or in combination with TNF etc. Also envisaged are further combinations of activators such as Protein A in combination with LPS, Protein A in combination with platelet-activating factor, Protein A in combination with unmethylated CpG oligodinucleotide, or in combination with TNF; or LPS in combination with any of the other activators mentioned above; or unmethylated CpG oligodinucleotide in combination with any of the other activators mentioned above; or TNF in combination with any of the other activators mentioned above. In a preferred embodiment, the activator is fMLP, or a combination of fMLP with one or more of the other activators mentioned above.

In a further embodiment of the present invention the analyte 12 may be a protein, preferably a lipocalin, in particular Human Neutrophil Lipocalin (HNL).

In a preferable embodiment the anti-analyte-antibody 24 is selected from the group of monoclonal and/or polyclonal antibody, in particular an antibody specific for binding HNL.

The device 100 is preferable a disposable cartridge. The cartridge 100 may be made of any kind of material as long as it is compatible with the detection to be performed on the sample. Preferred materials are glass or (transparent) plastic by injection moulding especially in view of disposability of such device 100 and/or cost during production. The main function of the device 100 is to provide an inlet in which an immunoassay can be performed to detect an analyte.

Figure 2:
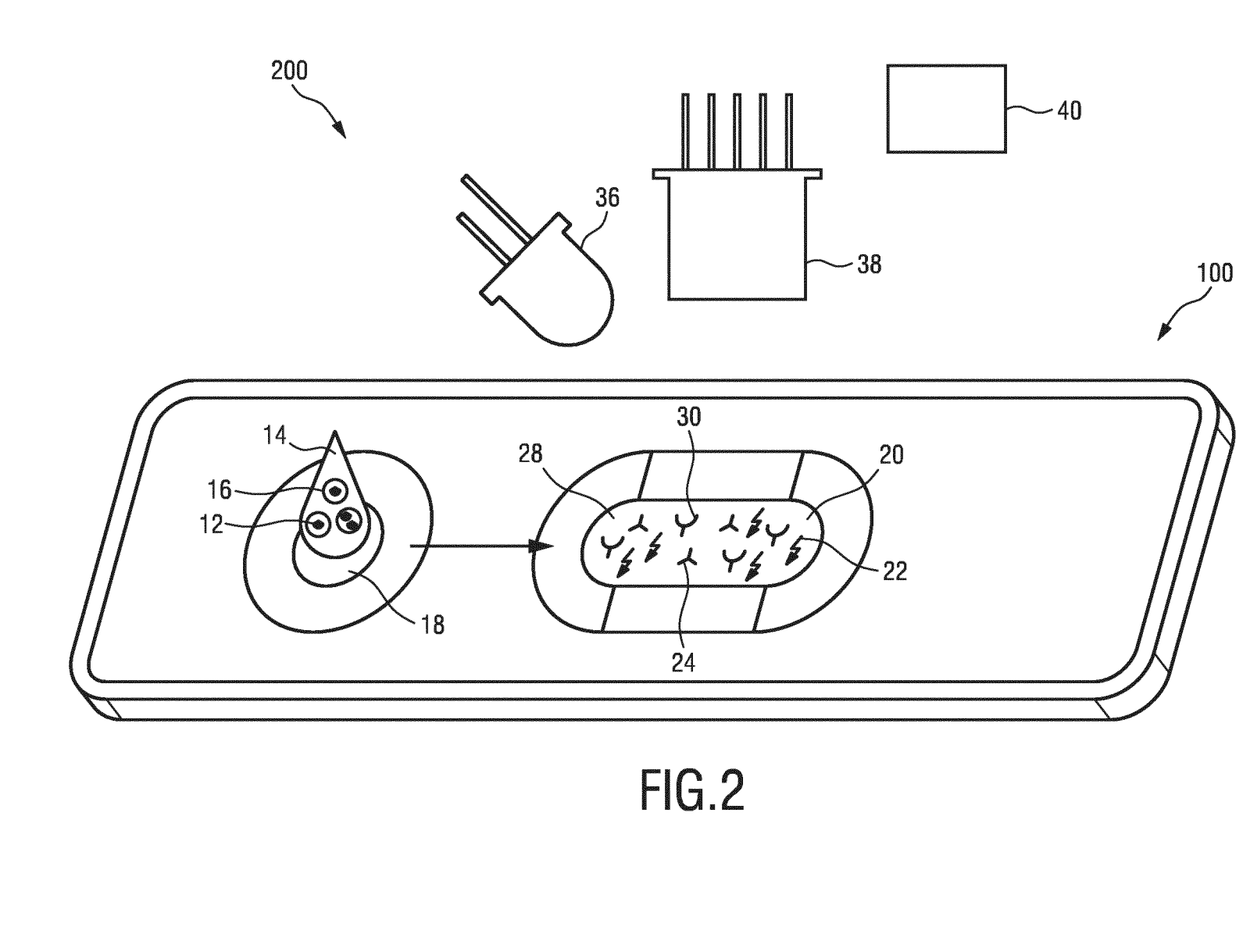
FIG. 2 shows a first embodiment of a system and device in accordance with the present invention.

FIG. 2 shows a first embodiment of a system 200 and device 100 in accordance with the present invention. In addition to the element of the first embodiment of the device 100 shown in FIG. 1, the first embodiment of the system 200 comprises a light source 36, a detection unit 38 and an analyzer 40.

The light source 36 projects light at the detection surface 28 of the immunoassay unit 20 of the device 100. The light ray hits a molecule, preferably the antibody-antigen-complex, and is scattered and/or reflected by the latter and finally detected by a detection unit 38. The light source 36 may for example be a laser diode or an LED.

In a preferable embodiment the light source 36 emitting light towards the detection surface 28, where it is totally internally reflected into a reflected light. The molecules in the immunoassay unit 20, especially the antibody-antigen-complex will lead to a frustrated total internal reflection (FTIR), which can be detected with the help of the detection unit 38. The measurement signals of this detector 38 are evaluated and analyzed by an analyzer 40.

The detection unit 38 receives reflected light from the detection surface 28 of the immunoassay unit 20. The detection unit 38 may for example comprise photodiodes, photo resistors, photocells, a CCD chip or a photo multiplier tube.

The analyzer 40 analyzes the reflected light by the detection unit 38. Therefore, the analyzer 40 determines the presence or absence as well as the concentration of an analyte 12 in a body fluid sample 14 containing a plurality of cells 16. In a preferably embodiment the body fluid sample 14 is a whole blood sample.

In a preferable embodiment the cartridge 100, which is constructed entirely from plastic components is disposable. It plugs into a hand-held unit the system 200 that contains the optical detection system, control electronics, software, e.g. electromagnets and a read-out display.

In a further preferable embodiment the cartridge 100 may be used as a rapid, robust and easy to use point-of-care immunoassay for small sample volumes. Wherein the analyzing is performed either directly at the bedside, or at the physician's office or even at home. Such a point of care test needs to have a fast total assay time (sample input, result output in a typical total assay time less than ten minutes).

The device 100 can further be used in automated high-throughput testing. In this case, the device is e.g. a well-plate or cuvette, fitting into an automated instrument.

Figure 3:
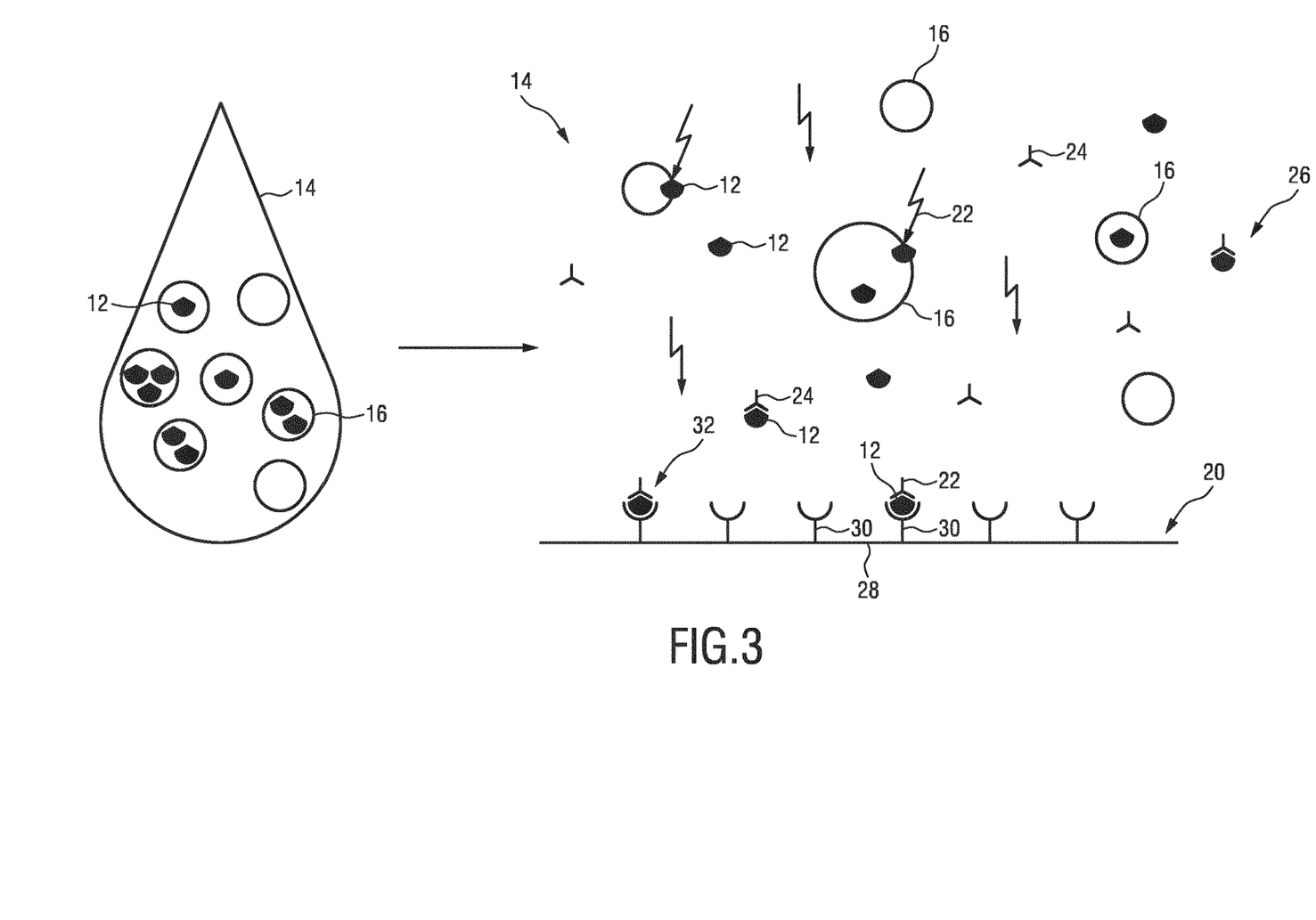
FIG. 3 shows a schematic drawing of the biochemical reactions proceeding in the device in accordance with the present invention.

FIG. 3 shows a schematic drawing of the biochemical reactions in the device 100 in accordance with the present invention. The drop represents the body fluid sample 14 which comprises a plurality of cells 16. The cells again comprise the analyte 12. Besides the cells the sample e.g. a whole blood sample comprises e.g. plasma (not shown).

When performing an immunoassay in a disposable cartridge 100 a number of process steps have to be done; e.g. filling, redispersion of the reagents, activation of the cells 16, binding to the anti-analyte-antibodies 24 and detection. Filling of the cartridge 100 (sample input 18 and immunoassay unit 20) can take up to one minute. Also the redispersion of the reagents and incubation takes typically 1 to 2 minutes. Before the immunoassay reaction (which is considered a rate-limit step) can start, already as much as half the assay time can be already spent. Because of the variation in body fluid samples 14 from different bodies the filling time will be different for every cartridge and body fluid sample 14. If the reagents used in the immunoassay unit 20 are provided in dry form, the activation of the cells 16 by the activating reagent 22 starts when the activating reagent 22 redisperse as soon as they come in contact withe the body fluid sample 14. The activating can proceed e.g. by binding on a specific receptor outside the cells and therefore activate a chemical cascade reaction inside the cells to release the analyte 12. After the release the cells are still active, viable and not been lysed. The activating step is important because it determines the amount of analyte 12, which can bind in the next step to the anti-analyte-antibody 24 to form a complex 26. Therefore, the activating step determines the total amount of binding as complex 26.

In a preferable embodiment the body fluid sample may be whole blood, the activating reagent may be fMLP, the analyte may be HNL and the antibodies may be anti-HNL-antibodies that is immunospecific for HNL. According to this embodiment the activating reagent fMLP stimulate the release of HNL by the neutrophils and prevent non-specific interaction of blood cells with the antibodies. After a fixed incubation time the amount initially present and released HNL are detected using antibodies specifically recognizing HNL. Detection of complexes formed between an anti-analyte-antibody and analyte present after activation in the body fluid sample may be accomplished by a variety of known techniques, such as radioimmunoassay (RIA) and enzyme linked immunosorbent assay (ELISA).

Suitable assays are well known in the art and are amply described in the scientific and patent literature (Harlow and Lane, 1988). Assays that may be used include, but are not limited to, the double monoclonal antibody sandwich immunoassay technique (U.S. Pat. No. 4,376,110); monoclonal-polyclonal antibody sandwich assays (Wide L., "Solid Phase Antigen-Antibody Systems," Radioimmunoassay Methods: European Workshop Sep. 15-17 1970 Edinburgh, Kirkham and Hunter, eds., (Churchill Livingston, Edenburgh, (1971)) pp. 405-412; the "western blot" method (U.S. Pat. No. 4,452,901); immunoprecipitation of labeled ligand (Brown et al., J. Biol. Chem. 4980-4983 m 1980); enzyme-linked immunosorbent assays; immunocytochemical techniques, including the use of fluorochromes (Brooks et al, CHn. Exp. Immunol, 39: 477, 1980); and neutralization of activity (Bowen-Pope et al., Science, 226:701-703, 1984). Other immunoassays include, but are not limited to, those described in U.S. Pat. Nos. 3,850,752; 3,901,654; 3,935,074; 3,984,533; 3,996,345; 4,034,074; and 4,098,876.

For detection purposes, an anti-analyte-antibody may either be labeled or unlabeled. Unlabeled antibodies may be used in agglutination assays or in combination with labeled detection reagents that bind to the immuno-complex (e.g., antiimmunoglobulin, protein G, Protein A or a lectin and secondary antibodies, or antigen-binding fragments thereof, capable of binding to the antibodies that specifically bind to the analyte). If the anti-analyte-antibody is labeled, the reporter group may be any suitable reporter group known in the art, including radioisotopes, fluorescent groups (e.g. fluorescein or rhodamine), luminescent groups, enzymes, biotin and dye particles. Labels that are themselves directly detectable include fluorescent or luminescent dyes, metals or metal chelates, electrochemical labels, radionuclides (e.g., 32P, 14C, 1251, 3H, or 1311), magnetic labels or beads (e.g., DYNABEADS), paramagnetic labels, or colorimetric labels (e.g., colloidal gold, colored glass or plastic beads). Such detectable labels may be directly conjugated to the anti-analyte-antibody or detection reagent or may be associated with a bead or particle that is attached to the anti-analyte-antibody. Labels that are detectable through binding of a labeled specific binding partner include biotin, digoxigenin, maltose, oligohistidine, 2,4-dinitrobenzene, phenyl arsenate, ssDNA, or dsDNA). Indirect labels that can be indirectly detected by their production of a detectable reaction product include various enzymes well known in the art, such as alkaline phosphatase, horseradish peroxidase, (3-galactosidase, xanthine oxidase, glucose oxidase or other saccharide oxidases, or luciferases, which cleave appropriate substrate to form a colored or fluorescent reaction product.

Figure 4A:
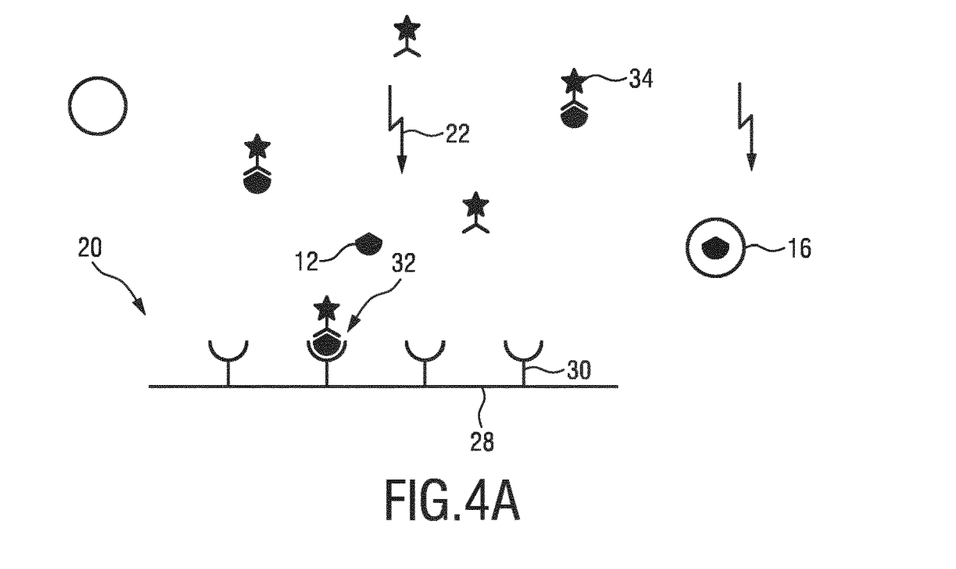
FIG. 4A shows a schematic drawing of the biochemical reactions proceeding in the device using magnetic particles in accordance with the present invention.

FIG. 4A shows a schematic drawing of the biochemical reactions proceeding in the device 100 using magnetic particles 34 in accordance with the present invention. In the embodiment the first anti-analyte-antibody 24 is coupled to a magnetic particle 34, while the second anti-analyte-antibody 30 is immobilized on a detection surface 28. The detection surface may be a solid support such as any material known to those of ordinary skill in the art to which the antibody may be attached.

After activation of the cells 16 to release the analyte 12, the analyte 12 can be bound in a first complex 26. At least partially simultaneous to the forming of the first complex 26, the second complex 32 can be formed by binding of the second anti-analyte-antibody 30 to the first complex 26 to form a second complex 32.

The anti-analyte-antibody may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent).

The magnetic particle with a diameter between about 50 to 2000 nm, particularly between about 250 and 750 nm and more particularly between 400 and 600, e.g. 500 nm are used for immunoassay as described in the present invention. This is advantageously because of the manipulating the bound anti-analyte-antibodies 24 inside the immunoassay unit 20. Therefore, the binding step to form the first and the second complex 26 and 32 can proceed faster. Optionally, the magnetic properties of the particle can also be used for detecting.

Therefore, the detection of magnetic particles may be based on optical properties such as the size of the particle itself (e.g. as measured in FTIR (Frustrated Total Internal Reflection)) or by adding chromophoric groups to the magnetic particle (e.g. a fluorescent polystyrene particle comprising magnetic material).

Figure 4B:
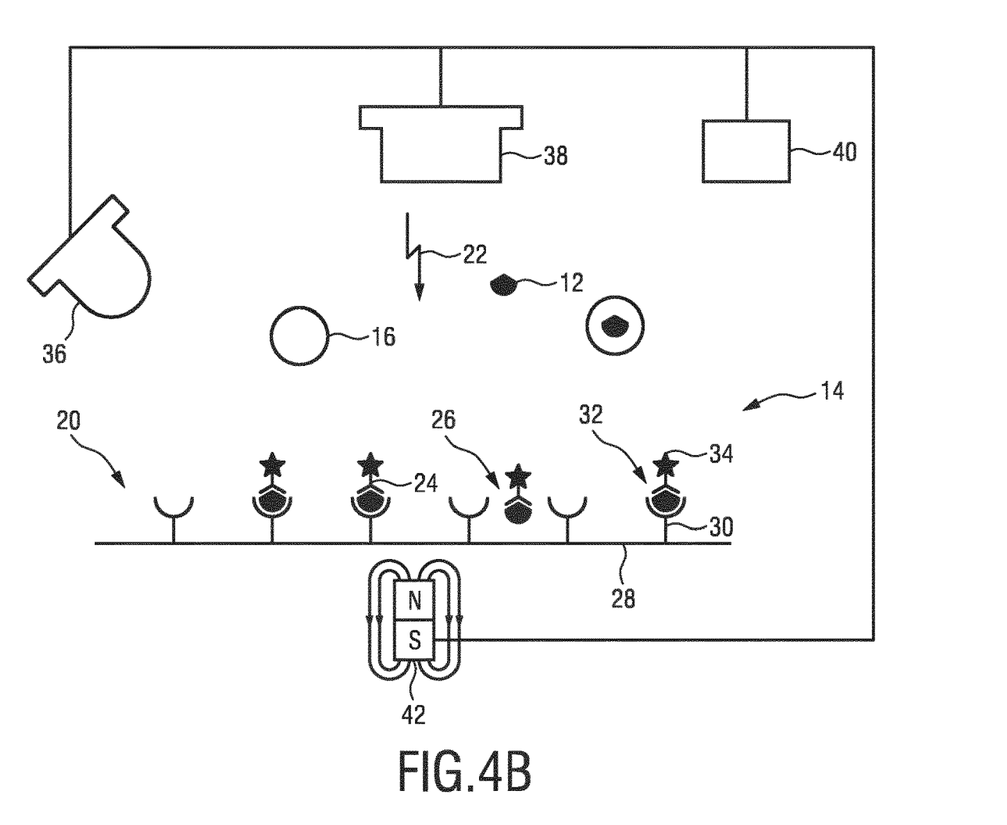
FIG. 4B shows a schematic drawing of the detection of magnetic particles in a sandwich immunoassay, in accordance with an embodiment of the present invention.

FIG. 4B shows a schematic drawing of the detection of magnetic particles in a sandwich immunoassay, in accordance with an embodiment of the present invention. Such embodiment typically comprises a light source 36 emitting light, a light detector 38 for detecting and measuring the reflected light, and connected thereto an analyzing unit 40 for evaluation of the information of the detection unit 38. The light is emitting into the immunoassay unit 20, which is typically located in the device 100, comprising a detection 28 surface made from glass or a transparent plastic. Further, the immunoassay unit 20 comprises the body fluid sample 14 to be tested and magnetic particles 34 which are functionalized with a first anti-analyte-antibody 24 for detection of the analyte 12 and which can be magnetically actuated by a magnetic field 42. After performing the immunoassay the presence of magnetic particles 34 at the detection surface 28 "frustrates" the total internal reflection of a light beam, resulting in a reduction of the reflected light proportional to the number of magnetic particles 34 located near or on the detection surface of the immunoassay unit.

In a preferable embodiment the disposable cartridge 100 automatically fills itself from a single drop of the body fluid sample 14 e.g. whole blood. Once filled, no other fluid movement is required. The entire immunoassay process within the immunoassay unit 20 is performed by externally applying magnetic field 42 to control the movement of magnetic particles 34 bound to the first anti-analyte-antibody 24 in the immunoassay unit 20. The magnetic particles 34 are preloaded into the immunoassay unit 20 during its manufacture and automatically disperse into the body fluid sample 14 as the cartridge 100 fills with a body fluid sample e.g. whole blood. After the cells 16 have released the analyte 12, the first anti-analyte-antibodies 24 coupled to the magnetic particle 34 bind to the target molecule 12 in the body fluid sample 14 and build the first complex 26. After a short time, preferable around a minute, a large fraction of the analyte 12 end up being bound as a first complex 26.

An electromagnet situated beneath the device 100 in the system 200 then generates a magnetic field that attracts all the magnetic particles 34 to the detection surface 28, which is coated with the second anti-analyte-antibody 30 that is able to bind to a second binding site on the analyte 12 to build the second complex 32. As a result of this magnetic attraction, the surface concentration of the analyte 12 is significantly increased, which speeds up the binding process. The analyte 12 ends up, bound in a "sandwich", between the first 24 and the second anti-analyte-antibody 30 as a second complex 32.

An electromagnet situated above (not shown) the immunoassay unit 20 then generates a magnetic field that pulls unbound magnetic particles away from the detection surface 28. In this way, a very fast and accurately controlled separation between bound and unbound magnetic particle is achieved, which can replace a washing step. Because each magnetic particle that remains on the surface 28 is bound there by an analyte 12, the number of magnetic particles 34 remaining at the surface 28 is a measure of the target molecule 12 concentration in the body fluid sample 14.

In the final phase, the number of bound second complex 32 is measured using e.g. an optical technique based on frustrated total internal refection. Illuminated at the correct angle, light from the light source 36 hitting the underside of the detection surface 28 is normally reflected without any loss in intensity. However, when magnetic particles are bound to the detection surface they scatter and absorb the light, reducing the intensity of the reflected light. These intensity variations in the reflected light, which correspond to the number of bound magnetic particles 32, are detected by a detection unit 38 preferable a CMOS image sensor. In the end the analyzer 40 analyze the reflected light and calculate the amount of analyte 12 in the body fluid sample 14.

In a preferable embodiment the analyzer 40 is coupled to a read-out display so the user can read out the result of the assay (not shown).

The detection of a complex of an analyte and an anti-analyte-antibody coupled to a magnetic particle are well known in the art. See, e.g. WO 2010/035204 A1 or WO 2008/107827 A1, the disclosure of which is incorporated herein by reference in its entirety.

FIG. 4B shows the schematic drawing of a "sandwich immunoassay". Therefore, two anti-analyte-antibodies are required. In a preferably embodiment (not shown) the antibody binding and therefore the analyte bound in a first complex is detected by a label on the first anti-analyte-antibody. In a further embodiment, the second anti-analyte-antibody is labeled.

Many means are known in the art for detecting binding in an immunoassay and are within the scope of the present invention. Antibodies: A Laboratory Manual (1988) by Harlow & Lane or more recent editions; Immunoassays: A Practical Approach, Oxford University Press, Gosling, J. P. (ed.) (2001) or more recent editions; and/or Current Protocols in Molecular Biology (Ausubel et al), which is regularly updated. Examples of such assays usually involve the antibody attached to a surface or matrix, body fluid sample added and time allowed for a first complex to form, followed by forming a second complex of a second anti-analyte-antibody bound to the first complex to allow detection of the complex (a sandwich ELISA) or a detectable version of an analyte to detect free analyte binding sites on the antibody surface (a competition ELISA).

If the analyte is HNL, the level of analyte, as detected by the foregoing methods, above a certain threshold is correlated with the presence of an inflammatory disease, and a level below said threshold indicates that the patient is unlikely to have an inflammatory disease. A patient is unlikely to have a bacterial infection disease when the HNL level is within the normal range. A patient is likely to have a bacterial disease when the HNL level exceeds the normal range.

Figure 5:
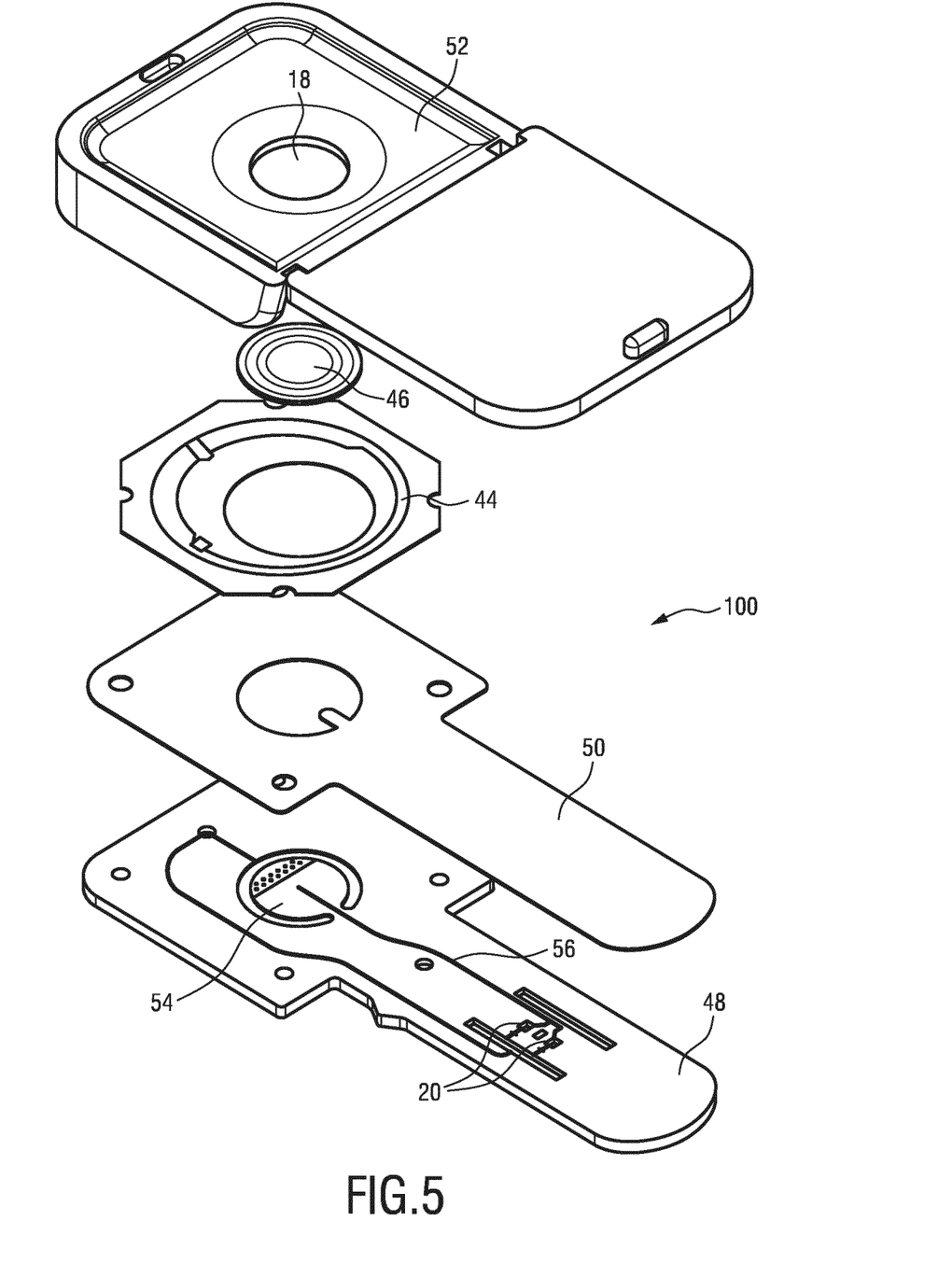
FIG. 5 shows a second embodiment of a device in accordance with the present invention.

FIG. 5 shows a second embodiment of a device 100 in accordance with the present invention. In addition to the element of the first embodiment of the device 100 shown in FIG. 1 the second embodiment of the device 100 comprises a RFID tag 44, a separating membrane 46, a base 48, a laminate foil 50 and a cover 52.

The RFID tag 44 may comprise a passive RFID component (antenna and read/write RFID tag) for storing data, such as calibration data, expiry date, type of tests, and for transmitting data to a reader comprised in the system; the RFID component is sealed between the laminate foil 50 and the cover 52;

The separation membrane 46 may act as a filter—membrane to separate interfering compounds of the body fluid sample. It is heat-sealed between the cover 52 and the foil 50/base 52.

The base 48 in which the body fluid sample is entirely capillary driven, comprising: a filter support 54; two immunoassay units 20 for performing an immunoassay of the body fluid sample, comprising the detection surface 28, optionally with the immobilized second anti-analyte-antibody 24 bound thereon; a micro fluidic path 56 between the filter support 54 and the immunoassay units 20; air venting arrangement to discharge air bubble from body fluid sample; on back face of the immunoassay units 20: transparent optical prism (not shown); a laminate foil 50, made of polymer, located between the RFID tag 44 and the base 48; the portions of the foils facing the immunoassay unit 20 have the reagents (incl. activating reagent, anti-analyte-antibody) attached thereto; the foil 50 is attached to the base 48 thanks to a single sided adhesive layer; a rigid cover 52 for handling the device 100, covering the RFID tag 44, provided with a hinging top plate for covering the sample input 18 (which is a hole provided through the rigid cover 52, the RFID tag 44 and the foil 50 to form a body fluid sample path to the base 48, via the filter 46).

EXAMPLE 1

Detection of HNL in a Whole Blood Sample from Patients with Bacterial or Viral Infections and from Healthy Patients.

An exemplary detection of HNL in a whole blood sample according to the invention is carried out on the Magnotechbio sensor system using a detection based on frustrated total internal reflection (FTIR). The system consists of a handheld analyzer instrument and a disposable self contained cartridge. All assay reagents necessary for the detection of HNL are contained in the cartridge. Once a droplet of the sample is applied, the sample is automatically drawn into the cartridge by capillary forces. There, the activating reagent fMLP (N-Formylmethionyl-leucyl-phenylalanine) stimulate the release of HNL by the neutrophils. Afterwards the magnetic nanoparticles functionalized with an anti-HNL-antibody bind to HNL and serve as labels for the detection. Magnetic forces are used to transport the magnetic particle to the detection surface, which is also functionalized with anti-HNL-antibodies to which the analyte as the first complex can bind. Magnetic actuation of the magnetic particles occurs via the alternate action of two magnets, e.g. an upper magnet (washing magnet) and a lower magnet (binding magnet). Light is projected on the surface of the cartridge at an angle that is slightly shallower than the critical angle, causing a reflection that is imaged on a camera sensor. When particles do bind on the detection surface some of the light is reflected and scattered resulting in a decreased intensity compared to a measurement in the absence of magnetic particles.

The magnetic particles have a diameter of 500 nm and are functionalized with monoclonal anti-N-HNL-antibodies and the detection surface was functionalized with monoclonal anti-C-terminal-HNL-antibodies.

A whole blood sample was added to the cartridge. Immediately after the sample is drawn into the cartridge actuation is started and the white blood cells were activated to release the analyte. After 8 minutes the analyte is detected as the second complex bound to both antibodies in a "sandwich" on the detection surface. Signal change resulting from the binding of the magnetic particles to de detection surface is proportional to the amount of HNL.

The concentration of HNL in whole blood after neutrophil activating with fMLP is increased in blood obtained from patients with bacterial infections as opposed to blood from healthy controls and blood from patients with viral infections.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A device for detecting an analyte in a body fluid sample, comprising:
    a sample input,
        wherein the sample input is arranged to receive the body fluid sample;
        and
    an immunoassay unit, the immunoassay unit comprising:
        a detection surface, wherein the detection surface is arranged to perform an immunoassay of the body fluid sample wherein the body fluid sample comprises a plurality of cells;
        a mobile activating reagent,
            wherein the activating reagent is arranged to activate the plurality of cells to release an analyte,
            wherein the activating reagent is able to activate the plurality of cells in order to release the analyte without lysing the plurality of cells themselves;
            and
        a mobile first anti-analyte-antibody, wherein the mobile first anti-analyte-antibody is capable of binding to the analyte released from the plurality of cells to form a first complex,
    wherein the mobile activating reagent and the mobile first anti-analyte-antibody are stored in a dry state within the immunoassay unit of the device;

wherein the mobile activating reagent and the mobile first anti-analyte-antibody are configured to be mixed with the body fluid sample;

wherein the first complex comprises the first anti-analyte-antibody and the analyte, wherein forming of the first complex proceeds at least partially simultaneous to the activating of the plurality of cells.

2. The device according to claim 1,
wherein the immunoassay unit further comprises a second anti-analyte-antibody,
wherein the second anti-analyte-antibody is immobilized on the detection surface,
wherein the second anti-analyte-antibody is able to bind to the analyte in the first complex to form a second complex,
wherein the second complex comprises the first anti-analyte-antibody, the analyte and the immobilized second anti-analyte-antibody,
wherein forming of the second complex proceeds at least partially simultaneous to the forming of the first complex.

3. The device according to claim 2, wherein the first anti-analyte-antibody and/or the second anti-analyte-antibody are selected from the group of monoclonal and/or polyclonal antibodies.

4. The device according to claim 2, wherein the first anti-analyte-antibody and/or the second anti-analyte-antibody are an antibody specific for binding human neutrophil lipocalin (HNL).

5. The device according to claim 1,
wherein the immunoassay unit further comprises a buffer reagent,
wherein the buffer reagent comprises a sugar, a salt, or a mixture thereof.

6. The device according to claim 5, wherein the sugar is a polysaccharide.

7. The device according to claim 6, wherein the polysaccharide, is selected from the group consisting of dextran, carboxymethyl dextran (CM-dextran) and a combination thereof.

8. The device according to claim 5, wherein the salt is selected from the group consisting of potassium bromide, potassium chloride, potassium iodide, potassium thiocyanate, and a combination thereof.

9. The device according to claim 5, wherein the buffer reagent comprises at least one reagent of sugar and salt.

10. The device according to claim 1, wherein the activating reagent is an N-formyl-peptide.

11. The device according to claim 1, wherein the analyte is a protein.

12. The device according to claim 1, wherein the mobile first anti-analyte-antibody is coupled to a magnetic particle.

13. The device according to claim 1, wherein the body fluid sample is a whole blood sample.

14. The device according to claim 1, wherein the activating reagent is an N-Formylmethionyl-leucyl-phenylalanine (fMLP) and/or Protein A and/or Lipopolysaccharide (LPS) and/or platelet-activating factor and/or an unmethylated cytosine-phosphorothioate-guanine (CpG) oligodinucleotide and/or tumor necrosis factor (TNF).

15. The device according to claim 1, wherein the analyte a lipocalin.

* * * * *